US008784839B2

(12) United States Patent
Heinz et al.

(10) Patent No.: US 8,784,839 B2
(45) Date of Patent: *Jul. 22, 2014

(54) ATTENUATED LIVE VACCINES

(75) Inventors: Franz Xaver Heinz, Vienna (AT); Christian Mandl, Vienna (AT)

(73) Assignee: Valneva Austria GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/048,412

(22) Filed: Mar. 15, 2011

(65) Prior Publication Data

US 2011/0165230 A1 Jul. 7, 2011

Related U.S. Application Data

(62) Division of application No. 10/450,649, filed as application No. PCT/AT02/00046 on Feb. 11, 2002, now Pat. No. 8,486,419.

(30) Foreign Application Priority Data

Feb. 21, 2001 (AT) .................................. A 272/2001

(51) Int. Cl.
*C12Q 1/70* (2006.01)
*C12N 15/09* (2006.01)

(52) U.S. Cl.
USPC ...................... 424/218.1; 424/278.1; 435/455

(58) Field of Classification Search
None
See application file for complete search history.

(56) References Cited

U.S. PATENT DOCUMENTS

| | | | |
|---|---|---|---|
| 6,184,024 B1 | 2/2001 | Lai et al. | |
| 7,094,411 B2 | 8/2006 | Kinney et al. | |
| 7,244,434 B2 | 7/2007 | Beer et al. | |
| 2004/0052818 A1 | 3/2004 | Heinz et al. | |
| 2010/0323003 A1 | 12/2010 | Heinz et al. | |

FOREIGN PATENT DOCUMENTS

| | | |
|---|---|---|
| EP | 1018556 | 7/2000 |
| WO | 90/11092 | 10/1990 |
| WO | 94/29469 | 12/1994 |
| WO | 97/47197 | 12/1997 |
| WO | 2009/098277 A1 | 8/2009 |

OTHER PUBLICATIONS

Thurner et al, (Journal of General Virology 2004, vol. 85, p. 1113-1124.*
Markoff Lewis et al. "A Conserved Internal Hydrophobic Domain Mediates the Stable Membrane Integration of the Dengue Virus Capsid Protein." Virology vol. 233, No. 1, 1997, pp. 105-177, XP002201374 Fig. 2.
Hope R. Graham. et al "Sequence Motifs Required for Lipid Droplet Association and Protein Stability are Unique to the Hepatitis C Virus Core Protein." Journal of General Virology, vol. 81 No. 8, Aug. 2000 pp. 1913-1925, XP00107721.
Kofer Regina M et al. "Capsid Protein C of Tick-Borne Encephalitis Virus Tolerates Large Internal Deletions and is a Favorable Target for Attenuation of Virulence." Journal of Virology, United States Apr. 2002. vol. 76. No. 7 Apr. 2002 pp. 3534-3543 XP001073714.
Peter Schlick et al., Helices α2 and α3 of West Nile Virus Capsid Protein are Dispensable for Assembly of Infectious Virions, Journal of Virology Jun. 2009, pp. 5581-5591.
Kofler et al. (PNAS 10192004): 1951-1956).
Aberle et al. (J. Virol. 29 (2005) 15107-15113.
Gherarch et al (J. Gen Virology 85 (2005), 2925-2936.
Mandl, et al. (In Vitro—Synthesized Infectious RNA as an Attenuated Live Vaccine in a Flavivirus Model) (Nature Medicine, vol. 4 (Dec. 1998) pp. 1438-1440.
Mandl (Viral Immunology, vol. 17, 2004, pp. 461-472).
Markoff. J. Virology, 1989, vol. 63, pp. 3345-3352.
Markoff et al. Virology, 1997. vol. 233, pp. 105-117.
Seligman et al., Live flavivirus vaccines: reasons for caution. Lancet. 2004, vol. 363, pp. 2073-2075.
Kofler et al., Spontaneous Mutations Restore the Viability of Tick-Borne Encephalitis Virus Mutants With Large Deletions in Protein C Journal of Virology, 2003, vol. 77, pp. 443-451.
Mandl. Flavivirus Immunization With Capsid-Deletion Mutants: Basics, Benefits, and Barriers Viral Immunology, 2004. vol. 17, pp. 461-472.
Bhamarapravati N. et al., Live Attenuated Tetravalent Detigue Vaccine. (2000) Vaccine 18, 44-47.
Kefler, R M, et al "Capsid Protein C of Tick-Borne Encephalitis Virus Tolerants Large Internal AH Deletions and is a Favorable Target of Attenuation of Virulence." Journal of Virology, vol. 76, No. 7 (2002) pp. 3534-3543.
Xiang, J., et al. "Full-Length GB Virus C (Hepatitis G Virus) RNA Transcripts are Infectious in Primary CD4-Positive T Cells." Journal of Virology. vol. 74. No. 19 (2000) pp. 9125-9133.
Kofler, R.M, et al. "Spontaneous Mutations Restore the Viability of Tick-Borne Encephalitis Virus Mutants with Large Deletions in Protein C." Journal of Virology, vol. 77, No. 1 (2003) pp. 443-451.
Kofler, R.M., et al. "Mimicking Live Flavivirus Immunization with a Noninfectious RNA Vaccine," PNAS, vol. 101, No. 7 (2004) pp. 1951-1956.
Ryan, M.D., et al. Virus-Encoded Proteinases of the *Flaviviridae*. Journal of General Virology, vol. 79 (1998) pp. 947-959.
Thiel, Heinz-Jurgen, et al. "Proteins Encoded in the 5' Region of the Pestivirus Genome-Considerations Concerning Taxonomy," Veterinary Microbiology, vol. 33 (1992) pp. 213-219.
Gruenberg, A., et al. "Processing of Dengue Virus type 2 Structural Proteins Containing Deletions in Hydrophobic Domains." J Arch Virol vol. 122 (1992) pp. 77-94.
Varnavski, A N., et al. "Noncytopathic Flavivirus Replicon RNA-Based System for Expression and Delivery of Heterologous Genes." Virology, No. 255 (1999) pp. 366-375.

(Continued)

*Primary Examiner* — Agnieszka Boesen
(74) *Attorney, Agent, or Firm* — Wolf, Greenfield & Sacks, P.C.

(57) ABSTRACT

Disclosed is an attenuated flavivirus live vaccine comprising a flavivirus mutant, characterized in that the flavivirus mutant has a deletion in the capsid protein of at least more than 4 successive amino acids, wherein the carboxy-terminal hydrophobic region is not affected by the deletion.

13 Claims, 4 Drawing Sheets

(56) References Cited

OTHER PUBLICATIONS

Mandl, C.W., et al. "Sequence of the Structural Proteins of Tick-Borne Encephalitis Virus AP (Western Subtype) and Comparative Analysis with Other Flaviviruses." Virology, vol. 166 (1998) pp. 197-205.

Björklund. H.V. et al. "Molecular Characterization of the 3' Noncoding Region of Classical Swine Fever Virus Vaccine Strains." Virus Genes 1998, 16(3), pp. 307-312.

Butrapet, Siritorn et al. "Attenuation Markers of a Candidate Dengue Type 2 Vaccine Virus, Strain 16681 (PDK-53), Are Defined by Mutations in the 5' Noncoding Region and Nonstructural Proteins 1 and 3." J. Virology 2000, 74(7), pp. 3011-3019.

Guirakhoo, F. et al. "Recombinant Chimeric Yellow Fever-Dengue Type 2 Virus Is Immunogenic and Protective in Nonhuman Primates." J. Virology 2000, 74(12), pp. 5477-5485.

Hall, Roy A et al. "Loss of Dimerisation of the Nonstructural Protein NS1 of Kunjin Virus Delays Viral Replication and Reduces Virulence in Mice, but Still Allows Secretion of NS1." Virology 1999, 264, pp. 66-75.

Hope, Graham R. and John McLauchlan. "Sequence Motifs Required for Lipid Droplet Association and Protein Stability are Unique to the Hepatitis C Virus Core Protein." J. General Virology 2000, 81, pp. 1913-1925.

Hopp, Thomas P. et al. "Prediction of Protein Antigenic Determinants from Amino Acid Sequences." Proc. Natl. Acad. Sci. USA 1981, 78(6), pp. 3824-3828.

Khromykh, A.A. et al. "RNA Binding Properties of Core Protein of the Flavivirus Kunjun." Arch. Virol. 1996, 141. pp. 685-699.

Khoraykh, A.A. et al. "Subgenomic Replications of the Flavivirus Kanjin: Construction and Applications," J. Virology, 1997, 71(2), pp. 1497-1505.

Kyle, Jack and Russell F. Doolittle. "A Simple Method for Displaying the Hydropathic Character of a Protein." J. Mol. Biol. 1982, 157, pp. 105-132.

Lai, C.J. et al. "Evaluation of Molecular Strategies to Develop a Live Dengue Vaccine." Clinical and Diagnostic Virology 1998, 10, pp. 173-179.

Mandl, Christian W. et al. "Attenuation of Tick-Borne Encephalitis Virus by Structure-Based Site-Specific Mutagenesis of a Putative FlavMrus Receptor Binding Site." J. Virology 2000, 74(20), pp. 9601-9609.

Mandl, Christian W. et al. "Spontaneous and Engineered Deletions in the 3' Noncoding Region of Tick-Borne Encephalitis Virus: Construction of Highly Attenuated Mutations of Flavivirus" J Virology 1998, 72(3), pp. 2132-2140.

Markoff, Lewis et al. "A Conserved Internal Hydrophobic Domain Mediates the Stable Membrane Integration of the Dengue Virus Capsid Protein." Virology 1997, 233, pp. 105-117.

McMinn, Peter C. "The Molecular Basis of Virulence of the Encephalitogenic flavivirus." J. General Virology 1997, 78, pp. 2711-2722.

Meyers, Gregor et al. "Mutations Abrogating the RNase: Activity in Glycoprotein Ems of the Pestivirus Classical Swine Fever Virus Lead to Virus Attenuation." J. Virology 1999, 73(12), pp. 10224-10235.

Nitayaphan, Sorachai et al. "Nuccotide Sequence of the Virulent SA-14 Strain of Japanese Encephalitis Virus and its Attenuated Vaccine Derivative, SA-14-14-2" Virology 1990,177, pp. 541-552.

Post, Apulo R. et al. "Heterogeneity in Envelope Protein Sequence and N-Linked Glycosytation among Yellow Fever Virus Vaccine Strains." Virology 1991, pp. 160-167.

Xie, Hong et al. "Mutation in NS5 Protein Attenuates Mouse Neurovirulence of Yellow Fever 17D Vaccine Virus." J. General Virology 1998, 79, pp. 1895-1899.

Appeal by Intervet EP1373478.

EPO Preliminary Opinion EP1373478.

Grounds for EPO Decision Upholding Patent in Unamended Form EP1373478.

Notice of Opposition of Intervet EP1373478 (Merck group).

Reply by Intercell AG EP1373478.

Response by Intercell to Intervet's Appeal EP1373478.

Mason, et al.; "Production and characterization of vaccines based on flaviviruses defective in replication"; Virology; 2006; 35(2): 432-443.

Patkar, et al.; "Functional Requirements of the Yellow Fever Virus Capsid Protein"; Journal of Virology; 2007; 81(12): 6471-6481.

Reimann; et al.; "Packaged replicons of bovine viral diarrhea virus are capable of inducing a protective immune response"; Virology; 2007; 366: 377-386.

Schlick, et al.; "Characterization of West Nile virus live vaccine candidates attenuated by capsid deletion mutations"; Vaccine; 2010; 28: 5903-5909.

Zhu, et al.; "Attenuated dengue 2 viruses with deletions in capsid protein derived from an infectious full-length cDNA clone"; Virus Research; 2007; 126: 226-232.

\* cited by examiner

CSF Virus

BVD Virus

BD Virus

FIG. 1B

HC Virus type 1

HC Virus type 2

HC Virus type 3

FIG. 2

TBE Virus

1 VKKAILKGKGGGPPRRVSKETATKTRQPRVQMPNGLVLMRMMGILWHAVAGTARNPVLKAFWNSVPLKQATAALRKIKRTVSALMVGLQKRGKRRSATDWMSWLLVITLLGMTLA 115

WN Virus

1 SKKPGGPGKNRAVNMLKRGMPRGLSLIGLKRAMLSLIDGKGPIRFVLALLAFFRFTAIAPTRAVLDRWRGVNKQTAMKHLLSFKKELGTLTSAINRRSTKQKKRGGTAGFTILLGLIACALLSK 124

Den Virus type 2

1 NDQRKKARNTPFNMLKRERNRVSTVQQLTKRFSLGMLQGRGPLKLFMALVAFLRFLTIPPTAGILKRWGTIKKSKAINVLRGFRKEIGRMLNILNRRRRTAGMIIMLIPTVMA 113

CSF Virus

1 SDDGASGSKDKKPDRMNKGKLKIAPREHEKDSKTKPPDATIVVEGVKYQIKKKGKVKGKNTQDGLYHNKNKPPESRKKLEKALLAWAVITILLYQPVAA 99

BVD Virus

1 SDTKEEGATKKKTQKPDRLERGKMKIVPKESEKDSKTKPPDATIVVEGVKYQVRKKGKTKSKNTQDGLYHNKNKPQESRKKLEKALLAWAIIAIVLFQVTMG 102

BD Virus

1 SDDNKNEKTNEKKPDRVKRGAMKITPKESEKDSKSKPPDATIVVDGVKYQVKKKGKVKSKNTQDGLYHNKNKPPESRKKLEKALLAWAVLAVLMWQPVKP 100

HC Virus type 1

1 STNPKPQKKNKRNTNRRPQDVKFPGGGQIVGGVYLLPRRGPRLGVRATR 49
50 KTSERSQPRGRRQPIPKARRPEGRTWAQPGYPWPLYGNEGCGWAGWLLSPRGSRPSWGPTDPRRRSRNLGKVIDTLTCGFADLMGYIPLVGAPLGGAARALAHGVRVLEDGVNYATGNLPGCSFSIFLLALLSCLTVPASA 190

HC Virus type 2

1 STNPKPQRKTKRNTNRRPQDVKFPGGGQIVGGVYLLPRRGPRLGVRATR 49
50 KTSERSQPRGRRQPIPKDRRSTGKSWGKPGYPWPLYGNEGLGWAGWLLSPRGSRPSWGPNDPRHRSRNVGKVIDTLTCGFADLMGYIPVVGAPLGGVARALAHGVRVLEDGVNFATGNLPGCSFSIFLLALLSCITTPVSA 190

HC Virus type 3

1 STLPKPQRKTKRNTIRRPQDVKFPGGGQIVGGVYVLPRRGPRLGVRATR 49
50 KTSERSQPRGRRQPIPKARRSEGRSWAQPGYPWPLYGNEGCGWAGWLLSPRGSRPSWGPNDPRRRSRNLGKVIDTLTCGFADLMGYIPLVGAPVGGVARALAHGVRALEDGINFATGNLPGCSFSIFLLALFSCLIHPAA 189

SEQUENCE LISTING

<160> NUMBER OF SEQ ID NOS: 9

<210> SEQ ID NO 1
<211> LENGTH: 115
<212> TYPE: PRT
<213> ORGANISM: Tick-borne encephalitis virus

<400> SEQUENCE: 1

Val Lys Lys Ala Ile Leu Lys Gly Lys Gly Gly Pro Pro Arg Arg
1               5                   10                  15

Val Ser Lys Glu Thr Ala Thr Lys Thr Arg Gln Pro Arg Val Gln Met
            20                  25                  30

Pro Asn Gly Leu Val Leu Met Arg Met Met Gly Ile Leu Trp His Ala
            35                  40                  45

Val Ala Gly Thr Ala Arg Asn Pro Val Leu Lys Ala Phe Trp Asn Ser
        50                  55                  60

Val Pro Leu Lys Gln Ala Thr Ala Ala Leu Arg Lys Ile Lys Arg Thr
65                  70                  75                  80

Val Ser Ala Leu Met Val Gly Leu Gln Lys Arg Gly Lys Arg Arg Ser
                85                  90                  95

Ala Thr Asp Trp Met Ser Trp Leu Leu Val Ile Thr Leu Leu Gly Met
            100                 105                 110

Thr Leu Ala
        115

<210> SEQ ID NO 2
<211> LENGTH: 124
<212> TYPE: PRT
<213> ORGANISM: West Nile virus

<400> SEQUENCE: 2

Ser Lys Lys Pro Gly Gly Pro Gly Lys Asn Arg Ala Val Asn Met Leu
1               5                   10                  15

Lys Arg Gly Met Pro Arg Gly Leu Ser Leu Ile Gly Leu Lys Arg Ala
            20                  25                  30

Met Leu Ser Leu Ile Asp Gly Lys Gly Pro Ile Arg Phe Val Leu Ala
            35                  40                  45

Leu Leu Ala Phe Phe Arg Phe Thr Ala Ile Ala Pro Thr Arg Ala Val
        50                  55                  60

Leu Asp Arg Trp Arg Gly Val Asn Lys Gln Thr Ala Met Lys His Leu
65                  70                  75                  80

Leu Ser Phe Lys Lys Glu Leu Gly Thr Leu Thr Ser Ala Ile Asn Arg
                85                  90                  95

Arg Ser Thr Lys Gln Lys Lys Arg Gly Gly Thr Ala Gly Phe Thr Ile
            100                 105                 110

Leu Leu Gly Leu Ile Ala Cys Ala Leu Leu Ser Lys
        115                 120

<210> SEQ ID NO 3
<211> LENGTH: 113
<212> TYPE: PRT
<213> ORGANISM: Denge virus

<400> SEQUENCE: 3

Asn Asp Gln Arg Lys Lys Ala Arg Asn Thr Pro Phe Asn Met Leu Lys
1               5                   10                  15

Arg Glu Arg Asn Arg Val Ser Thr Val Gln Gln Leu Thr Lys Arg Phe
            20                  25                  30

```
Ser Leu Gly Met Leu Gln Gly Arg Gly Pro Leu Lys Leu Phe Met Ala
        35                  40                  45

Leu Val Ala Phe Leu Arg Phe Leu Thr Ile Pro Pro Thr Ala Gly Ile
 50                  55                  60

Leu Lys Arg Trp Gly Thr Ile Lys Lys Ser Lys Ala Ile Asn Val Leu
 65                  70                  75                  80

Arg Gly Phe Arg Lys Glu Ile Gly Arg Met Leu Asn Ile Leu Asn Arg
                 85                  90                  95

Arg Arg Arg Thr Ala Gly Met Ile Ile Met Leu Ile Pro Thr Val Met
             100                 105                 110

Ala
```

<210> SEQ ID NO 4
<211> LENGTH: 99
<212> TYPE: PRT
<213> ORGANISM: Klassisches Schweinefieber-Virus

<400> SEQUENCE: 4

```
Ser Asp Asp Gly Ala Ser Gly Ser Lys Asp Lys Lys Pro Asp Arg Met
1                5                  10                  15

Asn Lys Gly Lys Leu Lys Ile Ala Pro Arg Glu His Glu Lys Asp Ser
                 20                  25                  30

Lys Thr Lys Pro Pro Asp Ala Thr Ile Val Val Glu Gly Val Lys Tyr
             35                  40                  45

Gln Ile Lys Lys Lys Gly Lys Val Lys Gly Lys Asn Thr Gln Asp Gly
         50                  55                  60

Leu Tyr His Asn Lys Asn Lys Pro Pro Glu Ser Arg Lys Lys Leu Glu
65                  70                  75                  80

Lys Ala Leu Leu Ala Trp Ala Val Ile Thr Ile Leu Leu Tyr Gln Pro
                 85                  90                  95

Val Ala Ala
```

<210> SEQ ID NO 5
<211> LENGTH: 102
<212> TYPE: PRT
<213> ORGANISM: Bovines virales Diarrhoe Virus

<400> SEQUENCE: 5

```
Ser Asp Thr Lys Glu Glu Gly Ala Thr Lys Lys Thr Gln Lys Pro
1                5                  10                  15

Asp Arg Leu Glu Arg Gly Lys Met Lys Ile Val Pro Lys Glu Ser Glu
                 20                  25                  30

Lys Asp Ser Lys Thr Lys Pro Pro Asp Ala Thr Ile Val Val Glu Gly
             35                  40                  45

Val Lys Tyr Gln Val Arg Lys Lys Gly Lys Thr Lys Ser Lys Asn Thr
         50                  55                  60

Gln Asp Gly Leu Tyr His Asn Lys Asn Lys Pro Gln Glu Ser Arg Lys
65                  70                  75                  80

Lys Leu Glu Lys Ala Leu Leu Ala Trp Ala Ile Ile Ala Ile Val Leu
                 85                  90                  95

Phe Gln Val Thr Met Gly
             100
```

<210> SEQ ID NO 6
<211> LENGTH: 100
<212> TYPE: PRT

<213> ORGANISM: Border Disease Virus

<400> SEQUENCE: 6

Ser Asp Asp Asn Lys Asn Glu Lys Thr Asn Glu Lys Lys Pro Asp Arg
1               5                   10                  15

Val Lys Arg Gly Ala Met Lys Ile Thr Pro Lys Glu Ser Glu Lys Asp
            20                  25                  30

Ser Lys Ser Lys Pro Pro Asp Ala Thr Ile Val Val Asp Gly Val Lys
        35                  40                  45

Tyr Gln Val Lys Lys Gly Lys Val Lys Ser Lys Asn Thr Gln Asp
    50                  55                  60

Gly Leu Tyr His Asn Lys Asn Lys Pro Pro Glu Ser Arg Lys Lys Leu
65                  70                  75                  80

Glu Lys Ala Leu Leu Ala Trp Ala Val Leu Ala Val Leu Met Trp Gln
                85                  90                  95

Pro Val Lys Pro
            100

<210> SEQ ID NO 7
<211> LENGTH: 190
<212> TYPE: PRT
<213> ORGANISM: Hepatitis C Virus 1

<400> SEQUENCE: 7

Ser Thr Asn Pro Lys Pro Gln Lys Lys Asn Lys Arg Asn Thr Asn Arg
1               5                   10                  15

Arg Pro Gln Asp Val Lys Phe Pro Gly Gly Gly Gln Ile Val Gly Gly
            20                  25                  30

Val Tyr Leu Leu Pro Arg Arg Gly Pro Arg Leu Gly Val Arg Ala Thr
        35                  40                  45

Arg Lys Thr Ser Glu Arg Ser Gln Pro Arg Gly Arg Arg Gln Pro Ile
    50                  55                  60

Pro Lys Ala Arg Arg Pro Glu Gly Arg Thr Trp Ala Gln Pro Gly Tyr
65                  70                  75                  80

Pro Trp Pro Leu Tyr Gly Asn Glu Gly Cys Gly Trp Ala Gly Trp Leu
                85                  90                  95

Leu Ser Pro Arg Gly Ser Arg Pro Ser Trp Gly Pro Thr Asp Pro Arg
            100                 105                 110

Arg Arg Ser Arg Asn Leu Gly Lys Val Ile Asp Thr Leu Thr Cys Gly
        115                 120                 125

Phe Ala Asp Leu Met Gly Tyr Ile Pro Leu Val Gly Ala Pro Leu Gly
    130                 135                 140

Gly Ala Ala Arg Ala Leu Ala His Gly Val Arg Val Leu Glu Asp Gly
145                 150                 155                 160

Val Asn Tyr Ala Thr Gly Asn Leu Pro Gly Cys Ser Phe Ser Ile Phe
                165                 170                 175

Leu Leu Ala Leu Leu Ser Cys Leu Thr Val Pro Ala Ser Ala
            180                 185                 190

<210> SEQ ID NO 8
<211> LENGTH: 190
<212> TYPE: PRT
<213> ORGANISM: Hepatitis C Virus 2

<400> SEQUENCE: 8

Ser Thr Asn Pro Lys Pro Gln Arg Lys Thr Lys Arg Asn Thr Asn Arg
1               5                   10                  15

Arg Pro Gln Asp Val Lys Phe Pro Gly Gly Gln Ile Val Gly Gly
            20                  25                  30

Val Tyr Leu Leu Pro Arg Arg Gly Pro Arg Leu Gly Val Arg Ala Thr
        35                  40                  45

Arg Lys Thr Ser Glu Arg Ser Gln Pro Arg Gly Arg Arg Gln Pro Ile
50                  55                  60

Pro Lys Asp Arg Arg Ser Thr Gly Lys Ser Trp Gly Lys Pro Gly Tyr
65                  70                  75                  80

Pro Trp Pro Leu Tyr Gly Asn Glu Gly Leu Gly Trp Ala Gly Trp Leu
                85                  90                  95

Leu Ser Pro Arg Gly Ser Arg Pro Ser Trp Gly Pro Asn Asp Pro Arg
            100                 105                 110

His Arg Ser Arg Asn Val Gly Lys Val Ile Asp Thr Leu Thr Cys Gly
        115                 120                 125

Phe Ala Asp Leu Met Gly Tyr Ile Pro Val Val Gly Ala Pro Leu Gly
    130                 135                 140

Gly Val Ala Arg Ala Leu Ala His Gly Val Arg Val Leu Glu Asp Gly
145                 150                 155                 160

Val Asn Phe Ala Thr Gly Asn Leu Pro Gly Cys Ser Phe Ser Ile Phe
                165                 170                 175

Leu Leu Ala Leu Leu Ser Cys Ile Thr Thr Pro Val Ser Ala
            180                 185                 190

<210> SEQ ID NO 9
<211> LENGTH: 189
<212> TYPE: PRT
<213> ORGANISM: Hepatitis C Virus 3

<400> SEQUENCE: 9

Ser Thr Leu Pro Lys Pro Gln Arg Lys Thr Lys Arg Asn Thr Ile Arg
1               5                   10                  15

Arg Pro Gln Asp Val Lys Phe Pro Gly Gly Gly Gln Leu Val Gly Gly
            20                  25                  30

Val Tyr Val Leu Pro Arg Arg Gly Pro Arg Leu Gly Val Arg Ala Thr
        35                  40                  45

Arg Lys Thr Ser Glu Arg Ser Gln Pro Arg Gly Arg Arg Gln Pro Ile
50                  55                  60

Pro Lys Ala Arg Arg Ser Glu Gly Arg Ser Trp Ala Gln Pro Gly Tyr
65                  70                  75                  80

Pro Trp Pro Leu Tyr Gly Asn Glu Gly Cys Gly Trp Ala Gly Trp Leu
                85                  90                  95

Leu Ser Pro Arg Gly Ser Arg Pro Ser Trp Gly Pro Asn Asp Pro Arg
            100                 105                 110

Arg Arg Ser Arg Asn Leu Gly Lys Val Ile Asp Thr Leu Thr Cys Gly
        115                 120                 125

Phe Ala Asp Leu Met Gly Tyr Ile Pro Leu Val Gly Ala Pro Val Gly
    130                 135                 140

Gly Val Ala Arg Ala Leu Ala His Gly Val Arg Ala Leu Glu Asp Gly
145                 150                 155                 160

Ile Asn Phe Ala Thr Gly Asn Leu Pro Gly Cys Ser Phe Ser Ile Phe
                165                 170                 175

Leu Leu Ala Leu Phe Ser Cys Leu Ile His Pro Ala Ala
            180                 185

ATTENUATED LIVE VACCINES

RELATED APPLICATIONS

This application is a divisional of application Ser. No. 10/450,649 filed on Oct. 23, 2003 now U.S. Pat. No. 8,486,419, which is International Application AT2002/000046 filed on Feb. 11, 2002, which designated the U.S., claims the benefit thereof and incorporates the same by reference.

FIELD OF THE INVENTION

The invention relates to attenuated flavivirus live vaccines.

BACKGROUND OF THE INVENTION

The family Flaviviridae comprises three genera, the genus flaviviruses, the genus pestiviruses, and the genus hepaciviruses.

The genus flaviviruses mainly includes viruses transmitted by mosquitoes or ticks, many of which are important pathogens of humans, and also of animals. Particularly important are the yellow fever (YF) virus, the Japanese encephalitis (JE) virus, the four serotypes of dengue (Den) viruses, the tick-borne encephalitis (TBE) virus, and also the West Nile (WN) virus which recently has also appeared in North America as a pathogen in humans and in various bird species.

The genus of pestiviruses contains animal pathogens of great economic importance, i.e. the classical porcine fever (CPF) virus, the bovine viral diarrhoea (BVD) virus and the border disease virus (BDV).

The genus hepaciviruses comprises the different subtypes of hepatitis C virus (HCV) and related viruses, such as the hepatitis G virus (HGV).

These three genera are combined in the family of Flaviviridae, since all representatives of this family have a nearly identical genome structure and show agreement in numerous structural and functional properties. All flaviviruses are relatively small, enveloped viruses which comprise a single-stranded RNA molecule with mRNA polarity as genome. The genome has a long open reading frame that codes for all proteins in the form of a polyprotein. The individual mature virus proteins are formed by the activity of viral and cellular proteases. The arrangement of the individual virus proteins in the genome is the same for all flaviviruses and starts at the 5' end with the capsid protein, the surface proteins and a series of non-structure proteins, the last of which is the viral polymerase. As a special feature, the pestiviruses furthermore contain an autoprotease in front of the capsid protein. The nucleocapsid of the flaviviruses is formed by just one single viral protein, i.e. the capsid protein, and surrounds the viral genome. The capsid is assumed to have an icosahedral symmetry.

The exact three-dimensional structure of the capsid protein is not yet known for any one of the flaviviruses. But the known amino acid sequences have numerous correlations, so that it is very likely that the capsid proteins will have numerous structural similarities. In this case, the similarities in representatives of the same genus naturally will be even greater than between representatives of different genera. In all instances, the capsid protein is a rather small protein having a length of approximately 100 to 190 amino acids. It has an unusually high portion of basic amino, acids, i.e. of the amino acids lysine and arginine. It is assumed that the basic amino acids are important for the interaction with the viral RNA (Khromykh and Westaway, 1996). Yet, all flavivirus capsid proteins also have characteristic hydrophobic sections (FIG. 1). Such a hydrophobic section always is formed by the carboxy-terminal approximately 20 amino acids. This section serves as an internal signal sequence for the surface structure protein following in the genome sequence. By this signal sequence which during protein syntheses is integrated in the membrane of the endoplasmatic reticulum, the capsid protein initially is anchored in the membrane. Later on, the anchor is proteolytically cleaved. In addition, there are internal hydrophobic sections. In representatives of the genus flaviviruses, the functional importance of an internal hydrophobic domain has been described (Markoff et al. 1997). The authors have indicated the borders of this domain for a series of flaviviruses as follows: dengue 1: 46-67, dengue 2: 46-66, dengue 3: 46-67, dengue 4: 45-65, Japanese encephalitis: 46-62, West Nile: 46-62, Murray Valley encephalitis: 46-62, Saint Louis encephalitis: 45-61, yellow fever: 43-58, Langat: 42-54, Powassan: 40-52, TBE: 42-54. Also for hepatitis C virus, a functionally important internal hydrophobic domain has been identified (Hope and McLauchlan, 2000), extending from amino acids 119 to 145, in particular from 125 to 144. Also pestiviruses have short internal sections of mainly hydrophobic character.

SUMMARY OF THE INVENTION

Vaccines have been successfully used against some flaviviruses. Thus, there are live vaccines against the YF virus, the JE virus and the CPF virus, and inactivated vaccines are employed against JE and TBE. In view of the great importance of the flaviviruses in human and veterinary medicine, there is a high demand in the development of new and improved vaccines.

A series of attenuated flaviviruses is known whose attenuation is based on mutations in various regions of the genome. Attenuating mutations have been observed either in naturally occurring strains, obtained by serial passages of viruses in the laboratory, prepared by selection of mutants in the presence of neutralizing antibodies or by the targeted introduction of mutations with the assistance of recombinant cloning techniques. There exist infectious cDNA clones of several flaviviruses, and the skilled artisan knows how to prepare such clones. With the assistance of these infectious cDNA clones, according to the prior art, mutations can be specifically introduced into the genome of flaviviruses.

Known mutations for attenuating flaviviruses are found in the following sections of the genome:

Envelope proteins: Most of the observations of attenuating mutations relate to the envelope protein E (genus flavivirus) (reviewed in McMinn, 1997; new e.g. Mandl et al., 2000). Likewise, attenuating mutations in protein E(rns) (genus pestivirus) have been described (Meyers et al., 1999).

Non-structure proteins: A point mutation in protein NS1 of the Kunjin virus led to a delayed replication and, thus, attenuation (Hall et al., 1999). Attenuating mutations have also been described in the proteins NS3 (Butrapet et al., 2000) and NS5 (Xie et al., 1998).

Non-encoding genomic section: Attenuation of the TBE virus by deletions in the 3'-terminal non-encoding region has been described (Mandl et al., 1998). With dengue viruses, experimental vaccines having deletions both in the 5' and in the 3' non-encoding regions have been prepared (Lai et al., 1998). It is assumed that the molecular basis of the attenuation of these viruses is the adverse effect on the viral replication by these mutations.

The present invention now has as its object to provide further possible ways of attenuating flaviviruses, which will give rise to live vaccines which primarily are suitable for the prophylaxis of flavivirus-caused diseases.

According to the invention, this object is achieved by an attenuated flavivirus live vaccine, comprising a flavivirus mutant which is characterised in that the flavivirus mutant has a deletion in the capsid protein of at least more than 4 successive amino acids, wherein the carboxy-terminal hydrophobic region is not affected by the deletion. Although—as mentioned above—a series of attenuated flaviviruses has already been described in the prior art, whose attenuation is based on mutations, so far in none of the cases mutations, in particular deletions, in the capsid protein have been described as the basis of the attenuation of flaviviruses. It was also completely surprising that flaviviruses which contain the mutation according to the invention in the capsid protein, lead to a reliable attenuation of flaviviruses and can be employed as flavivirus live vaccines. For, despite the inventive mutation provided in the capsid protein, a propagation of the attenuated virus may take place in the vaccinated subject after administering the virus according to the invention as live vaccine. This results in a series of advantages over inactivated vaccines.

DETAILED DESCRIPTION OF CERTAIN EMBODIMENTS OF THE INVENTION

Deletions in the capsid protein constitute a completely new attenuating principle for flaviviruses. So far, the capsid protein has never been considered as a relevant object in the art. Therefore, the finding of the present invention that the described deletion mutants in fact successfully lead to attenuated flavivirus live vaccines which are resistant to reverting to the virulent phenotype and thus are excellently suited for a broad application on humans has been the more surprising.

For the preparation of conventional inactivated vaccines it is necessary to produce large amounts of infectious and virulent virus. Also with recombinantly prepared inactivated vaccines, large amounts of antigen must be produced and purified. With a live vaccine, the amounts to be produced are substantially smaller, since the vaccine itself is propagated within the body of the vaccinated subject, whereby the production costs of live vaccines in general are substantially lower than those of inactivated vaccines. Moreover, not a virulent, but an apathogenic virus is produced, and therefore the production does not involve a health risk. Conventional inactivated flavivirus vaccines are prepared by inactivating infectious particles by a treatment with formalin, causing a certain change of the antigen structure. In the vaccinated subject, primarily a humoral immune response to structure proteins whose antigen structure does not exactly correspond to the native form is induced, and not an immune response to non-structure proteins whose importance, however, is very high for the build-up of a long-lasting immunity and for the formation of cytotoxic T cells.

In contrast, with the vaccine according to the invention a humoral and cellular immune response to surface and non structure proteins present in their completely native form and produced in vivo can be achieved, whereby, according to the present state of the art, a substantially longer-lasting protective immune response can be achieved than with an inactivated vaccine.

The inventive attenuated flavivirus live vaccine, particularly according to the preferred embodiments thereof, moreover has still further advantages over the conventional live vaccines and experimental live vaccines prepared by genetical engineering methods:

The presently used flavivirus live vaccines have been passaged in the laboratory many times, which has led to a plurality of mutations whose meaning for the biology of these viruses in detail has not yet been completely understood and whose respective contribution to the attenuation of these viruses, as well as the interaction between the individual attenuated mutations are not yet completely known (for JE, cf. Nitayaphan et al., 1990; for YF, cf. Post et al., 1992; for CPF, cf. Bjorklund et al., 1998). Some mutations are also located in antigens which are particularly important for the immune response, such as surface protein E. Therefore, certain antigen determinants are present in an altered form as compared to the wild-type virus. The complexity of the genetic basis of the attenuation of these viruses does not allow for the principles forming the basis of the attenuation to be directly applied to other flaviviruses.

In contrast, in the vaccine according to the invention only defined and generally applicable attenuated mutations are introduced in the capsid protein, whereby it is not necessary to change a protein which is particularly important for the immune response (the envelope protein or certain non-structural proteins, such as NS1 in genus flavivirus).

Preferred embodiments of the live vaccine according to the invention thus do not comprise any further mutations, particularly not in the envelope proteins as well as in other proteins involved in the immune response.

As has been also already mentioned above, a series of genetically engineered attenuated flaviviruses have been described in which the attenuation is based on point mutations. For these it is relatively easy to revert genetically. Also the reversion of a virus, attenuated by point mutation, to a virulent phenotype by a second point mutation has been described (Mandl et al., 2000). In contrast, in the live vaccine according to the invention, the attenuation is achieved by a deletion the reversion of which to the wild-type is impossible.

In further described cases, the attenuation is based on changes in the envelope proteins important to the immune response, or in sections of the genome which are important for replication and translation. Neither a change in the antigen structure of envelope proteins, nor a substantial adverse effect on the replication or translation are desirable if an immune response as natural and efficient as possible is to be elicited. These disadvantages are overcome, by the present invention in which merely an inner structural component, yet not any envelope proteins, non-structural proteins or regulatory non-encoding sections have been changed.

In a further set-up, flavivirus vaccines have been prepared by combining various viruses (chimeric viruses) (Guirakhoo et al., 2000). Since chimeric viruses are organisms in which genes of pathogenic viruses are newly combined with each other in a non-naturally occurring manner, the release of such viruses by vaccination harbours the risk of these chimeric viruses developing to new viruses the properties of which cannot be predicted. In contrast, the new vaccine does not constitute a combination of various virus genomes, and therefore it is not possible that a release by vaccination could cause the formation of a hitherto not naturally occurring virus species.

The introduction of the deletions of the invention into the capsid protein of flaviviruses, e.g., by aid of recombinant techniques, is possible for any skilled artisan by using methods known per se without undue experimental burden. The gene section coding for the respective capsid protein is known for all flaviviruses whose genomic sequence has been clarified to date, and for new flavivirus sequences it can be determined easily by sequence comparison. Of course, the deletions in this case must not lead to any shifting of the reading frame so that the carboxy-terminal hydrophobic region would be affected by the deletion. It is essential for this carboxy-terminal hydrophobic region to be largely maintained, and thus not to be affected by the deletion. With the techniques mentioned it is possible to prepare mutant, infectious viruses in the propagation of which all viral proteins, except for the capsid protein, are formed in native form. Replication and translation of these viruses then will not, or not essentially, be restricted. By propagation in cell cultures, preparations can be produced from these viruses which can be used as vaccine. In contrast to the unchanged wild-type virus, the viruses according to the invention, after having been inoculated into an appropriate host organism, exhibit an attenuated phenotype, i.e. they do not cause a disease. Yet they induce the formation of a specific immune response. A host organism immunized with the inventive flavivirus live vaccine will be protected from a subsequent infection with the virulent wild-type, i.e. in contrast to the unprotected organism, a disease caused by the wild-type virus will not occur.

The inventive deletion in the region of the capsid protein will be particularly well suited for preparing a mutant suitable as a live vaccine if attention is paid to a number of characteristics by aid of which the properties of the vaccine can be improved in the preparation of a mutant suitable as a vaccine. The deletions to be provided according to the invention in any event must be larger than 4 amino acids so as to prepare suitable attenuated immunogenic viruses, because viruses having deletions of up to 4 amino acids still exhibit a virulent phenotype similar to the wild-type virus. Moreover, it is only as of a deletion of this order that a reversion to the virulent virus type can be excluded.

Furthermore, the deletions according to the invention must not regard the carboxy-terminal hydrophobic region of the capsid protein. It is known that this sequence is necessary for the correct formation of the envelope protein following in the genome, and that it is removed from the mature capsid protein by proteolytic cleavage. The length of this signal sequence varies between individual flaviviruses, yet it can easily be determined by establishing hydrophilicity profiles (cf. FIG. 1). Accordingly, the deletion according to the invention must not involve this carboxy-terminal region.

The carboxy-terminal hydrophobic region relates at least to all the amino acids in this region which have a hydrophilicity score according to FIG. 1 of −1 and less. Particularly preferably, the C-terminal region having a hydrophilicity of below 0, according to FIG. 1, remains unchanged.

Preferred deletions according to the invention concern regions of internal hydrophobic domains. From FIG. 1 it can be seen that the capsid sequences of all flaviviruses, in addition to the above-indicated hydrophobic signal sequence at the carboxy terminus, furthermore contain sections of predominantly hydrophobic character in the midst of otherwise predominantly hydrophilic amino acid chains. Deletions by which regions of these internal domains are partially or completely removed will give rise to particularly suitable attenuated flavivirus live vaccines. As "internal hydrophobic domain" at least all those regions can be considered which have a negative hydrophilicity score in FIG. 1.

In FIG. 2, particularly preferred hydrophobic regions which may be at least partially deleted in a vaccine according to the invention are characterised for a number of flaviviruses. These regions can be determined by calculating the hydrophobicity profile of the respective amino acid sequences. The regions underlined in FIG. 2 have been calculated with the algorithm of Kyte and Doolittle (1982) with a window size of 5. Alternatively, hydrophobic regions can also be calculated with window sizes of between 5 and 13 amino acid residues, or by other algorithms, such as those of Hopp and Woods (1981), wherein usually window sizes of between 3 and 11 can be chosen.

The hydrophilicity blots according to FIG. 1 have been calculated according to the algorithms of Kyte and Doolittle (1982) with a window size of 9 amino acid residues, or of Hopp and Woods (1981), respectively, with a window size of 7 amino acid residues. Preferred hydrophobic regions are chosen from dengue 1: 46-67, dengue 2: 46-66, dengue 3: 46-67, dengue 4: 45-65, Japanese encephalitis: 46-62, West Nile: 46-62, Murray Valley encephalitis: 46-62, Saint Louis encephalitis: 45-61, yellow fever: 43-58, Langat: 42-54, Powassan: 40-52, TBE: 42-54, and HCV: 119-145, in particular 125-144.

A particular embodiment of the attenuated vaccine are capsid deletions which remove such large portions of an internal hydrophobic domain that the resulting mutant genomes do not produce viruses capable of being passage in a cell culture. These genomes can replicate and can efficiently translate all the proteins except for the capsid protein in native form, and possibly they can also form non-infectious subviral particles. By introducing additional point mutations or insertions which increase the hydrophobicity of the capsid protein, such deletion mutants can be made into virus mutants capable of being passaged and suitable as live vaccines. These insertions are sequences which differ from the originally deleted sequence. Suitable additional mutations may, e.g., be generated and identified in that the deletion mutants which are no longer capable of replication in a cell culture system, are introduced into a more sensitive propagation system (e.g. laboratory mice for viruses of the genus flaviviruses, the natural hosts for the pestiviruses, pig, sheep, cattle or chimpanzee in case of the hepatitis C virus) than the cell culture, and in that appropriate mutations are generated and selected by passaging in this system. In this ease, particularly preferred more sensitive systems are animals, in particular mice, rats, rabbits, hares, pigs, sheep, cattle or primates, e.g. chimpanzees. The resulting virus mutants constitute a particularly safe vaccine, since any reversion of the additional mutation would give rise to viruses incapable of propagation or capable of propagation to a very limited extent only. A reversion of the deletion is impossible a priori.

Preferred attenuated flavivirus live vaccines comprise a flavivirus mutant which have a deletion of from 5 to 70, preferably 6 to 25, in particular 7 to 20, successive amino acids in the capsid protein. Deletions of this preferred order each are characterised by qualitatively changed properties in their attenuation passaging behaviour. If the deletions are larger than 20 successive amino acids, a loss of the passaging capacity may occur during the preparation of the live vaccine in host cells. Such a missing passaging capacity property will depend on the sensitivity of the host cells, yet it may be restored for the respective host cells by certain additional mutations. The restoration may be by one or more mutations with which the hydrophobicity of the capsid protein is increased. Such further mutations preferably are selected from point mutations by which the hydrophobicity of the capsid protein is increased, or by introducing insertions of amino acid sections having predominantly hydrophobic properties into the capsid protein gene. Duplications of hydrophobic regions of the capsid protein have proved to be particularly favourable. Particularly preferred point mutations comprise the swapping of charged, or hydrophilic aminoacids, respectively (such as, e.g., aspartic acid, glutamic acid, lysine, arginine, histidine, tryptophane, glutamine, asparagine, tyrosine, serine, etc.) to less polar amino acids or non-polar amino acids (such as, e.g., isoleucine, leucine, phenylalanine, methionine, alanine, valine etc.). Such additional mutations are particularly preferably automatically generated by introduction into the more sensitive system. The selection of these additional mutations also occurs automatically by restoring the passaging capacity itself.

Often a single mutation which results only in a gradual difference in the polarity of the amino acid will suffice to restore the passaging capacity (e.g. exchanging proline for leucine or valine for phenylalanine).

Preferably, the deletions may reach as far as to 15 amino acids to the amino terminus and/or as far as to immediately in front of the beginning of the carboxy-terminal signal sequence. Although it has been assumed so far that the first 20 amino acids of the flavivirus capsid protein (or of the genomic section coding for this amino acid) were absolutely necessary for replication (Khromykh and Westaway, 1997), within the scope of the present invention also viruses capable of replication and of propagation, having deletions which extend into this region, could successfully be prepared.

The present invention is applicable to all representatives of flaviviruses. Within the scope of this application, the term "flaviviruses" thus relates to all the representatives of the family Flaviviridae, except where it is expressly pointed out that only the representatives of the genus flavivirus is meant. Particularly preferred representatives of flaviviruses with which the present invention is realised are selected from the group consisting of yellow fever virus, the Japanese encephalitis virus, the four serotypes of dengue viruses, tick-borne encephalitis virus, West Nile virus, Murray Valley encephalitis virus, Saint Louis encephalitis virus, Powassan virus, classical porcine fever virus, bovine viral diarrhoea virus, border disease virus, hepatitis C virus and hepatitis G virus. These representatives are particularly suitable for the present invention because of their known pathogenicity for humans and animals, since for these representatives the demand for a suitable attenuated live vaccine is particularly high.

For the live vaccine according to the invention only a slight amount of virus is necessary for an efficient immunisation so that, per administration, $10^1$ to $10^7$, preferably $10^2$ to $10^6$, in particular $10^3$ to $10^5$, infectious units of flaviviruses are sufficient with the live vaccine according to the invention. Preferably, the live vaccine can be administered as a single dose with this amount of infectious units.

Preferably, the live vaccine according to the invention comprises further active substances or auxiliary substances. Particularly preferred is the addition of antibiotics, such as neomycin or kanamycin, preservatives, such as thiomersal, and stabilizers, such as human albumin, lactose-sorbit, sorbit-gelatine, polygeline or salts, such as $MgCl_2$ or $MgSO_4$. In general, preferably amino acids, polysaccharides and (buffer) salts may be used as the additives.

In the preparation of the live vaccine according to the invention, it is recommendable—if it is to be administered to humans—to use non-transformed host cells, since in this manner both, the risk of a change of properties (e.g. an easy introduction of new, undesired mutations), and the risk of contaminations with components of these cells is avoided.

According to a further aspect of the present invention, the flavivirus vaccine may also be provided as a nucleic acid vaccine, the nucleic acid coding for a capsid protein deleted according to the invention. Preferably, such a nucleic acid flavivirus vaccine contains aminoglycoside antibiotics, such as neomycin or kanamycin, as is recommended by the FDA for plasmid vaccines, in addition to the nucleic acid. In the prior art, a whole-series of the most varying strategies has been described for vaccination with "naked" nucleic acids (cf. e.g. WO 90/11092, WO 94/29469, WO 97/47197, incorporated herein by reference, liposome-mediated nucleic acid transfer, preferably nucleic acid transfer with (preferably biodegradable) microspheres, . . . ).

Furthermore, the present invention also relates to a method of preparing the live vaccine according to the invention, which is characterised by the following steps:

providing a flavivirus or a flavivirus nucleic acid, wherein the flavivirus or the flavivirus nucleic acid comprises an inventive deletion in the capsid protein, propagating the flavivirus or the flavivirus nucleic acid in suitable host cells, recovering the virus particles propagated by the host cells, and working up the virus particles to a live vaccine.

Preferred host cells are selected from chicken embryo cells, primary chicken embryo cells, human diploid cell lines (e.g. WI-38, MRC-5) vero cells, primary hamster kidney cells, primary canine kidney cells or diploid fetal rhesus lung cells.

Finally, the present invention also relates to the use of a flavivirus nucleic acid which has an inventive deletion in the capsid protein, for preparing a vaccine for the prevention of flavivirus infections.

The invention will be explained in more detail by way of the following Examples as well as by the drawing figures to which, however, it shall not be restricted.

BRIEF DESCRIPTION OF THE DRAWINGS

FIGS. 1A-1C show hydrophilicity profiles of the capsid proteins of 3 representatives each of the 3 genera of the family Flaviviridae. Negative values indicate regions with predominantly hydrophobic character. The carboxy-terminal hydrophobic region is the signal sequence for the envelope protein following in the genome. For each protein, the hydrophilicity has been calculated and illustrated by way of example once according to the algorithm of Kyte and Doolittle (1982) with a window size of 9 amino acid residues (top) and once according to the algorithm of Hopp and Woods (1981) with a window size of 7 amino acid residues (bottom).

FIG. 2 shows the sequence alignment of the capsid proteins of 3 representatives each of the 3 genera of the family Flaviviridae. Sequence sections having predominantly hydrophobic character (determined according to Kyte and Doolittle with a window size of 5) have been underlined. In this instance, the respective most carboxy-terminally arranged section represents the signal sequence for the subsequent envelope protein. In this section there must not be any deletions. The other (internal) hydrophobic sections represent preferred regions for attenuating deletions.

EXAMPLES

Example 1

The Use of a Capsid Deletion Mutant of the TBE Virus as a Live Vaccine

In case of the TBE virus, the pathogenicity and immunogenicity may be examined in the adult mouse model. As the live vaccine, a mutant (CD28-43) of the TBE virus having a deletion of 16 amino acids in the region of the capsid protein was used. This and other mutants discussed in the following Examples are summarized in Table 1. Mutant CD28-43 exhibits a gene expression comparable to the wild-type virus and may be passaged as often as desired in BHK-21 cells. The mutant was prepared by introducing the respective mutation into the infectious cDNA clone of the TBE virus. RNA from this mutant cDNA clone was transcribed in vitro, and this RNA was electroporated in BHK-21 cells. 3 days later the cell culture supernatant was harvested, and the virus was twice passaged in baby mouse brains so as to obtain a high-titer virus suspension. The latter was used to examine the suitability of the mutant as a live vaccine in the adult mouse model. For this purpose, 10 five week old mice each were inoculated subcutaneously with 10,000 pfu of the mutant or of the virulent wild-type virus, and the survival rates were observed over a period of 4 weeks. As is apparent from Table 2, in the case of the virulent wild-type virus, 9 of the 10 mice died with the typical clinical signs of the encephalitis. In contrast thereto, none of the mice inoculated with the capsid deletion mutant died. Also when inoculating with a 100-fold higher dose with the mutant, none of the 10 mice became ill. This result means that the capsid deletion mutant was apathogenic. An assay of the serum samples of all the mice inoculated with the mutant showed that all had formed a specific immune response to the TBE virus. By inoculating with a higher dose of virulent virus, it was tested whether or not this immune response could protect against the infection with the wild-type virus. All the mice survived this challenge without any signs of a disease. This result means that the capsid deletion mutant had elicited a protective immunity and therefore can be used as a vaccine against the wild-type virus.

Example 2

Recovery of a Mutant Capable of being Passaged, which Mutant has a Deletion Extending into the Region of the Amino-Terminal 20 Amino Acids With the assistance of the infectious cDNA clone, a deletion was introduced in the capsid protein of the TBE virus, which deletion extended from amino acid 16 to amino acid 25 (mutant CD16-25; cf. Table 1). Mutant CD16-25 could be passaged as often as desired in a cell culture. This result indicates that, in contrast to the former state of the art, deletions extending into the region of the 20 amino-terminal amino acids, inclusive of the amino acid 16, do not destroy the replication of flaviviruses.

Example 3

Virulent Capsid Deletion Mutants

Figure 1A:
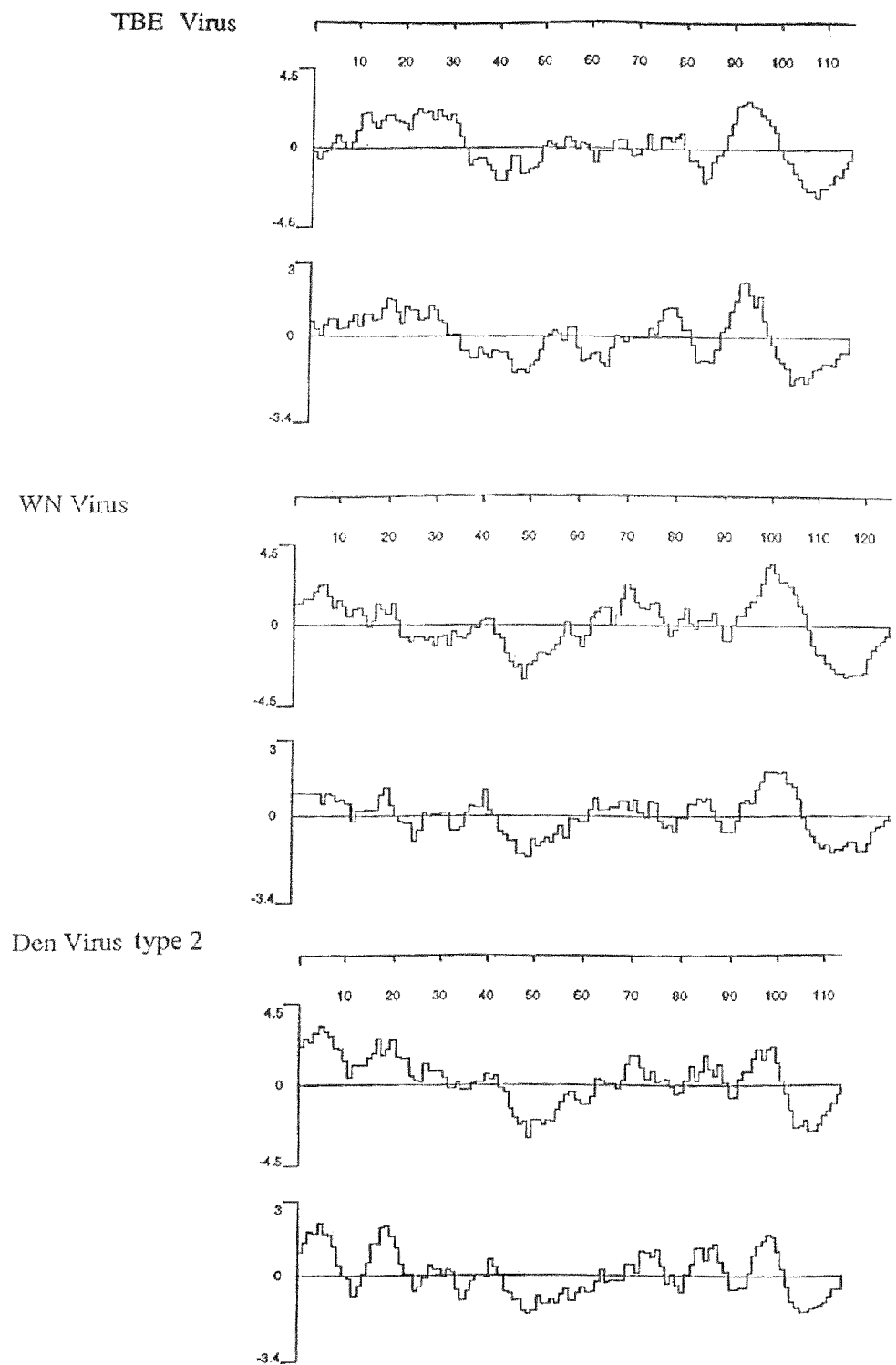
Figure 1B:
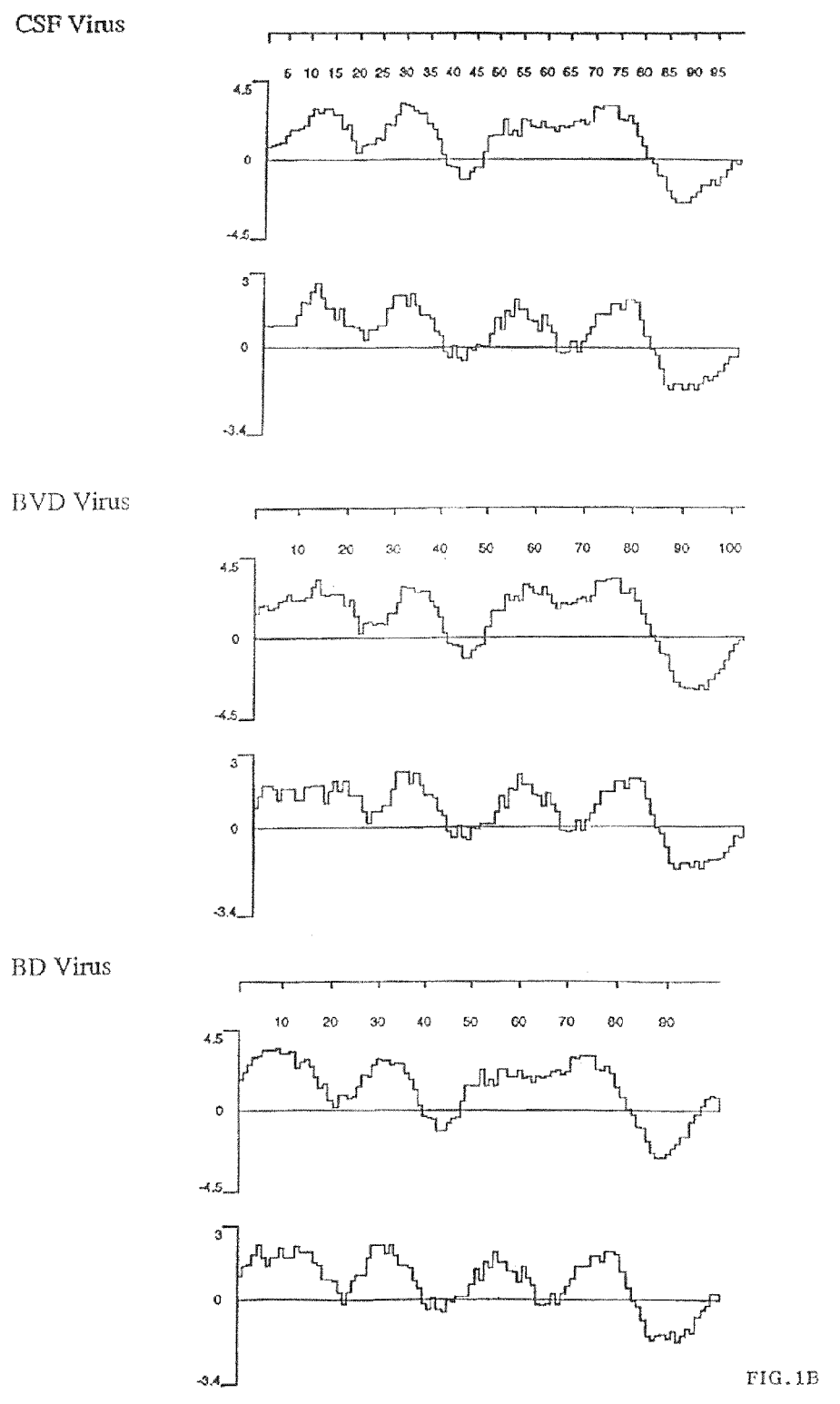
Figure 1C:
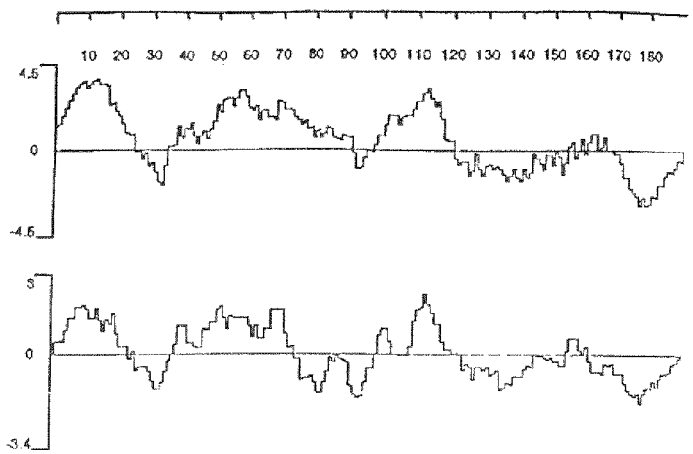
Figure 1C:
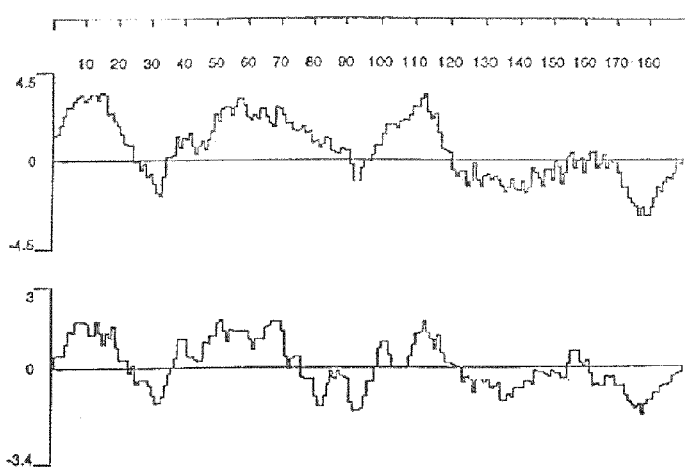
Figure 1C:
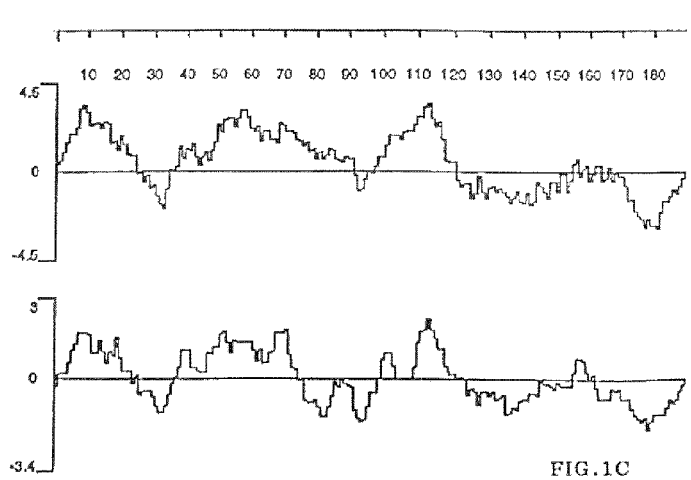

The capsid mutants CD28 and CD28-31 carry deletions of a length of 1 and 4 amino acids, respectively (Table 1). In these mutants, the deleted amino acids are not part of an internal hydrophobic domain (FIG. 1). Inoculation of this mutant in adult mice showed that they have a virulent phenotype corresponding to the wild-type virus and killed 80%, and 100%, respectively, of the mice (Table 2). This result indicates that deletions up to a size of 4 amino acids in non-hydrophobic regions of the capsid protein are not suitable for preparing an attenuated vaccine.

Example 4

Attenuated Capsid Deletion Mutants

The capsid deletion mutants CD28-35, CD28-39, and the mutant CD28-43 described in Example 1 carry deletions having a length of 8, 12 and 16 amino acids (Table 1). These deletions remove parts of an internal hydrophobic domain (FIG. 1). Inoculations of these mutants in adult mice showed that they have an attenuated phenotype, i.e. killed none, or in case of mutant CD28-35, only 10% of the mice (Table 2). This result shows that deletions removing parts of an internal hydrophobic domain lead to an attenuation. The extent of the attenuation will also depend on the size of the deletion and may be increased by enlargement thereof. All mice immunized with these attenuated mutants were completely protected against an infection by the virulent wild-type virus. This result confirms the result of Example 1 that the capsid deletion mutants can be used as live vaccines.

Example 5

Identification of Additional Mutations

The capsid deletion mutants CD28-48, CD28-54 and CD28-89 carry deletions having a length of 21, 27 and 62 amino acids (Table 1). These deletions remove an internal hydrophobic domain entirely, or in case of the largest deletion, all the internal hydrophobic sections of the capsid protein (FIG. 1). These mutants exhibit an undisturbed gene expression, yet they are not capable of being passaged in BHK-21 cells. Supernatants of BHK-21 cell cultures transfected with these mutants were harvested after 3 days and intracranially inoculated in 10 baby mice each (1 day old). This constitutes the most sensitive one of the known propagation systems for the TBE virus. After 5 to 10 days, in the case Of mutant CD28-48 all, in the case of mutant CD28-54 7 of the 10 baby mice died with clear clinical signs of the encephalitis. None of the mice inoculated with mutant CD28-89 died. In the brains of all the deceased mice, the TEE virus could be detected by PCR, whereas no virus could be found in the surviving mice. Virus from the brains of deceased mice could be passaged as often as desired in BHK-21 cell cultures. This result indicates that in mutants which had lost their passaging capacity in cell culture by removal of a hydrophobic domain, revertants can be selected which again are capable of being passaged in cell culture.

To determine the genetic basis of these changes, the genomic section coding for the capsid protein was sequenced for a series of such revertants. It has been shown that in each case, a further mutation in protein C was present in addition to the originally introduced deletion. These were point mutations or a sequence duplication. The additional mutations are summarized in Table 3. One common characteristic of all these mutations is that they increase the hydrophobicity of the capsid protein. The result shows that mutations which increase the hydrophobicity of the capsid protein are capable of reverting the effect of deletions of internal hydrophobic sequences as regards the passaging capacity of flaviviruses in cell cultures.

Example 6

Capsid Deletion Mutants with Additional Mutations as Live Vaccine

With the assistance of the infectious clone, two mutants were prepared which contained a deletion having a length of 21 amino acids of the internal hydrophobic domain together with one additional mutation each (selected from the mutations listed in Table 3) in the capsid protein. In contrast to the corresponding deletion mutant without an additional mutation (CD28-43), these two mutants, CD28-43/L70 and CD28-43/Du8, were capable of being passaged as often as desired (Table 1). This result confirms the results of Example 5. Inoculation of these mutants in adult mice showed that both were apathogenic and elicited a protective immunity (Table 2). This result indicates that mutants with deletions and additional mutations according to the above-described points of view are suitable as live vaccine.

TABLE 1

Capsid deletion mutants of the TBE virus

| Designation | Deletion[a] | Additional mutation | Genexpression[b] | Passaging capacity[c] |
|---|---|---|---|---|
| CD28 | Q28 | | + | + |
| CD28-31 | Q28-V31 | | + | + |
| CD28-35 | Q28-N35 | | + | + |
| CD28-39 | Q28-L39 | | + | + |
| CD28-43 | Q28-M43 | | + | + |
| CD28-46 | Q28-L46 | | + | + |
| CD28-48 | Q28-H48 | | + | − |
| CD28-54 | Q28-A54 | | + | − |
| CD28-89 | Q28-L89 | | + | − |
| CD16-25 | R16-K25 | | + | + |
| CD28-48/L70 | Q28-H48 | Q70->L | + | + |
| CD28-48/Du8 | Q28-H48 | I78-L85 Dupl[d] | + | + |

[a]Indicated are the first and the last deleted amino acid. The numbers refer to the position of the AA, counted from the amino terminus of the capsid protein.
[b]Determined by immunofluorescence staining of BHK-21 cells with TBE-specific antisera. + = immunofluorescence staining of comparable intensity as the wild-type virus; − = no staining.
[c]Determined by multiple transfer of cell culture supernatants to BHK-21 cells: + capable of being passaged; − not capable of being passaged.
[d]Duplication of the 8 amino acids of positions 78 to 85.

TABLE 2

Immunisation of adult mice

| Inoculum | Amount[a] | surviving[b] | protectively immunised[c] |
|---|---|---|---|
| wild-type | 10[4] pfu | 1/10 | n.a. |
| CD28 | 10[4] pfu | 0/10 | n.a. |
| CD28-31 | 10[4] pfu | 2/10 | n.a. |
| CD28-35 | 10[4] pfu | 9/10 | 9/10 |
| CD28-39 | 10[4] pfu | 10/10 | 10/10 |
| CD28-43 | 10[4] pfu | 10/10 | 10/10 |
| CD28-43 | 10[6] pfu | 10/10 | 10/10 |
| CD28-48/L70 | 10[4] pfu | 10/10 | 10/10 |
| CD28-48/Du8 | 10[4] pfu | 10/10 | 10/10 |

[a]Amount of the subcutaneously applied inoculum, indicated in plaque forming units (pfu) per mouse.
[b]Number of surviving mice/total number of mice
[c]Number of immunised mice/total number of mice. Immunisation was determined by means of the detection of TBE-specific antibodies in the serum. By a subsequent infection with virulent wild-type virus it was confirmed that immunisation completely protected against the disease. n.a. = not applicable

TABLE 3

Compensating mutations in capsid deletion mutants

| RNA[a] | Protein[b] |
|---|---|
| A299->U | D56->I |
| C302->U | P57->L |
| G328->U | V66->F |
| A341->U | Q70->L |
| C347->U | T72->I |
| A368->U | K79->I |
| C374->U | T81->M |
| A401->U | Q90->L |
| 364-387 Dupl[c] | I78-L85 Dupl |
| 307-363 Dupl | L59-K77 Dupl |

[a]Nucleotide positions in the genome of the TBE virus (GenBank No. U27495)
[b]Amino acid position in protein C
[c]Duplication of the indicated section

REFERENCES

1. Bjorklund, H. V., T. Stadejek, Vilcek, and S. Belak. 1998. Molecular characterization of the 3' noncoding region of classical swine fever virus vaccine strains. Virus Genes 16:307-312
2. Butrapet, S., C. Y. Huang, D. J. Pierro et al. 2000. Attenuation markers of a candidate dengue type 2 vaccine virus, strain 16681 (PDK-53), are defined by mutations in the 5' non-coding region and nonstructural proteins 1 and 3. J. Virol. 74:3011-3019.
3. Guirakhoo, F., R. Weltzin, T. J. Chambers et al. 2000. Recombinant chimeric yellow fever-dengue type 2 virus is immuno genic and protective in nonhuman primates. J. Virol. 74:5477-5485.
4. Hall R. A., A. A. Khromykh, J. M. Mackenzie, et al., 1999. Loss of dimerisation of the nonstructural protein NS1 of Kunjin virus delays viral replication and reduces virulence in mice, but still allows secretion of NS1. Virology 264:66-75.
5. Hope, R. G., and J. McLauchlan. 2000. Sequence motifs required for lipid droplet association and protein stability are unique to the hepatitis C virus core protein. J. Gen. Virol. 81:1913-1925.
6. Hopp, T. P., and K. R. Woods. 1981. Prediction of protein anti-genic determinants from amino acid sequences. PNAS 78:3824-3828.
7. Khromykh, A. A., and E. G. Westaway. 1996. RNA binding properties of core protein of the flavivirus Kunjin. Arch. Virol. 141:685-699.
8. Khromykh, A. A., and E. G. Westaway. 1997. Subgenomic replicons of the flavivirus Kunjin: construction and applications. J. Virol. 71:1497-1505.
9. Kyte, J., and R. F. Doolittle. 1982. A simple method for displaying the hydropathic character of a protein. J. Mol. Biol. 157:105-132.
10. Lai, C. J., M. Bray, R. Men, A. Cahour et al. 1998. Evaluation of molecular strategies to develop a live dengue vaccine. Clin Diagn. Virol. 10:173-179.
11. Mandl, C. W., Allison, S. L., Holzmann, H. et al. 2000. Attenuation of tick-borne encephalitis virus by structure-based site-specific mutagenesis of a putative flavivirus receptor binding site. J. Virol. 74:9601-9609.
12. Mandl, C. W., H. Holzmann, T. Meixner, S. Rauscher, P. F. Stadler, S. L. Allison, and F. X. Heinz 1998. Spontaneous and engineered deletions in the 3' noncoding region of tick-borne encephalitis virus: Construction of highly attenuated mutants of a flavivirus. J. Virol. 72: 2132-2140.
13. Markoff, L., B. Falgout, and A. Chang. 1997. A conserved internal hydrophobic domain mediates the stable membrane integration of the dengue virus capsid protein. Virology 233:105-117.
14. McMinn, P. C. 1997. The molecular basis of virulence of the encephalitogenic flaviviruses. J. Gen. Virol. 78:2711-2722.
15. Meyers, G., A. Saalmuller, and M. Buttner. 1999. Mutations abrogating the Rnase activity in glycoprotein E(rns) of the pestivirus classical swine fever virus lead to virus attenuation. J. Virol. 73:10224-10235.
16. Nitayaphan, S., J. A. Grant, G.-J. J. Chang, and D. W. Trent. 1990. Nucleotide sequence of the virulent SA-14 strain of Japanese encephalitis virus and its attenuated derivative, SA-14-14-2. Virology 177:541-552.
17. Post, P. R., C. N. D. Santos, R. Carvalho, A. C. R. Cruz, C. M. Rice, and R. Galler. 1992. Heterogeneity in envelope protein sequences and N-linked glycosylation among yellow fever virus vaccine strains. Virology 188:160-167.
18. Xie, H., K. D. Ryman, G. A. Campbell, and A. D. Barrett. 1998. Mutation in NS5 protein attenuates mouse neurovirulence of yellow fever 17D vaccine virus. J. Gen. Virol. 79:1895-1899.

The invention claimed is:
1. An attenuated tick-borne encephalitis virus (TBE virus) live vaccine comprising a TBE virus mutant, wherein the TBE virus mutant has a deletion in the capsid protein of
    (a) 5 to 20 successive amino acids, or
    (b) more than 20 successive amino acids, wherein the capsid protein additionally comprises one or more further mutations by which the hydrophobicity of the capsid protein is increased, the further mutation being selected from
        i) point mutations by which the hydrophobicity of the capsid protein is increased, and/or
        ii) insertions of amino acid sections having predominantly hydrophobic properties, and
    wherein the deletion concerns regions of the internal hydrophobic domain of the capsid protein and wherein the carboxy-terminal hydrophobic region is not affected by the deletion.

2. The TBE virus live vaccine according to claim 1 wherein 5 to 20 or up to 70 successive amino acids in the capsid protein are deleted.

3. The TBE virus live vaccine according to claim 1, wherein the insertions of amino acid sections having predominantly hydrophobic properties are duplications of hydrophobic regions of the capsid protein.

4. The TBE virus live vaccine according to claim 1, wherein the vaccine comprises $10^1$ to $10^7$, $10^2$ to $10^6$ or $10^3$ to $10^5$ infectious units of TBE virus.

5. The TBE virus live vaccine according to claim 1, wherein the vaccine further comprises antibiotics, preservatives, stabilizers, buffer substances or mixtures thereof.

6. The TBE virus live vaccine according to claim 5, wherein the vaccine comprises neomycin, kanamycin, thimerosal, human albumin, lactose-sorbitol, sorbitol-gelatin, polygeline, $MgCl_2$, $MgSO_4$, amino acids, polysaccharides, buffer salts or mixtures thereof.

7. The TBE virus live vaccine according to claim 1, wherein the vaccine is produced in non-transformed host cells.

8. A tick-borne encephalitis virus (TBE virus) vaccine, wherein the vaccine comprises a nucleic acid which codes for a deleted capsid protein that comprises a deletion of
    (a) 5 to 20 successive amino acids, or
    (b) more than 20 successive amino acids, wherein the capsid protein additionally comprises one or more further mutations by which the hydrophobicity of the capsid protein is increased, the further mutation being selected from
        i) point mutations by which the hydrophobicity of the capsid protein is increased, and/or
        ii) insertions of amino acid sections having predominantly hydrophobic properties, and
    wherein the deletion concerns regions of the internal hydrophobic domain of the capsid protein and wherein the carboxy-terminal hydrophobic region is not affected by the deletion.

9. The TBE virus vaccine according to claim 8, wherein the vaccine further comprises aminoglycoside antibiotics, neomycin, kanamycin, liposomes, microspheres or mixtures thereof.

10. A method of producing an attenuated tick-borne encephalitis virus (TBE virus) live vaccine comprising a TBE virus mutant according to claim 1, comprising the following steps:
    providing a TBE virus or a TBE virus nucleic acid, wherein the TBE virus or the TBE virus nucleic acid has a deletion in the capsid protein and further mutations as defined in claim 1,
    propagating the TBE virus or the TBE virus nucleic acid in suitable host cells,
    recovering the virus particles propagated by the host cells, and
    working up the virus particles to a live vaccine.

11. The method according to claim 10, wherein the host cell is selected from the group consisting of chicken embryo cells, primary chicken embryo cells, human diploid cell lines, vero cells, primary hamster kidney cells, primary canine kidney cells or diploid fetal rhesus lung cells.

12. The TBE virus live vaccine according to claim 2, wherein 6 to 20 or up to 25 successive amino acids in the capsid protein are deleted.

13. The TBE virus live vaccine according to claim 12, wherein 7 to 20 successive amino acids in the capsid protein are deleted.

* * * * *